US008986735B2

(12) United States Patent
Schobel et al.

(10) Patent No.: US 8,986,735 B2
(45) Date of Patent: Mar. 24, 2015

(54) SOLID DOSAGE FORM CONTAINING A TASTE MASKED ACTIVE AGENT

(75) Inventors: Alexander M Schobel, Whitehouse Station, NJ (US); Shyam S Vangala, Pine Brook, NJ (US)

(73) Assignee: Novartis AG, Basel (CH)

( * ) Notice: Subject to any disclaimer, the term of this patent is extended or adjusted under 35 U.S.C. 154(b) by 1585 days.

(21) Appl. No.: 11/724,410

(22) Filed: Mar. 15, 2007

(65) Prior Publication Data

US 2007/0292515 A1    Dec. 20, 2007

Related U.S. Application Data

(60) Provisional application No. 60/783,189, filed on Mar. 16, 2006.

(51) Int. Cl.
| | |
|---|---|
| *A61K 9/14* | (2006.01) |
| *A61K 47/00* | (2006.01) |
| *A61K 31/19* | (2006.01) |
| *A61K 31/192* | (2006.01) |
| *A61K 9/00* | (2006.01) |

(52) U.S. Cl.
CPC ............... *A61K 31/192* (2013.01); *A61K 9/006* (2013.01); *Y10S 514/825* (2013.01); *Y10S 514/974* (2013.01)
USPC ........... 424/487; 424/439; 424/484; 424/485; 424/486; 424/488; 514/570; 514/769; 514/781; 514/825; 514/974

(58) Field of Classification Search
CPC .... A61K 31/192; A61K 9/006; A61K 9/0056
USPC ................. 424/484, 485, 486, 487, 488, 439; 514/570, 769, 781, 825, 974
See application file for complete search history.

(56) References Cited

U.S. PATENT DOCUMENTS

| | | | |
|---|---|---|---|
| 4,145,440 A | 3/1979 | Fitch et al. | |
| 4,361,580 A | 11/1982 | Peck et al. | |
| 5,019,563 A | 5/1991 | Hunter et al. | |
| 5,024,997 A | 6/1991 | Motola et al. | |
| 5,032,384 A | 7/1991 | Yeh et al. | |
| 5,262,179 A | 11/1993 | Gregory et al. | |
| 5,416,181 A | 5/1995 | Nguyen | |
| 5,597,583 A | 1/1997 | Grattan | |
| 5,629,003 A | 5/1997 | Horstmann | |
| 5,633,006 A * | 5/1997 | Catania et al. ................. | 424/441 |
| 5,895,789 A * | 4/1999 | Gentile et al. ................. | 514/570 |
| 5,948,430 A | 9/1999 | Zerbe | |
| 6,090,401 A | 7/2000 | Gowan et al. | |
| 6,159,498 A | 12/2000 | Tapolsky et al. | |
| 6,177,096 B1 | 1/2001 | Zerbe | |
| 6,197,348 B1 | 3/2001 | Morella et al. | |
| 6,284,264 B1 | 9/2001 | Zerbe | |
| 6,419,903 B1 | 7/2002 | Xu | |
| 6,592,887 B2 | 7/2003 | Zerbe | |
| 6,596,298 B2 | 7/2003 | Leung | |
| 6,627,214 B1 | 9/2003 | Bunick et al. | |
| 6,656,493 B2 | 12/2003 | Dzija | |
| 6,923,981 B2 | 8/2005 | Leung | |
| 7,025,983 B2 | 4/2006 | Leung | |
| 7,067,116 B1 | 6/2006 | Bess | |
| 7,407,669 B2 | 8/2008 | Leung | |
| 2002/0169212 A1 | 11/2002 | Stroble et al. | |
| 2004/0043134 A1 * | 3/2004 | Corriveau et al. ............ | 426/658 |
| 2004/0116528 A1 | 6/2004 | Haas | |
| 2004/0156885 A1 | 8/2004 | Zerbe | |
| 2004/0208931 A1 * | 10/2004 | Friend et al. .................. | 424/471 |
| 2005/0031675 A1 | 2/2005 | Spence et al. | |
| 2005/0118217 A1 * | 6/2005 | Barnhart et al. .............. | 424/401 |
| 2005/0163830 A1 | 7/2005 | Rademacher et al. | |
| 2006/0198885 A1 * | 9/2006 | Dharmadhikari et al. .... | 424/464 |

FOREIGN PATENT DOCUMENTS

| | | |
|---|---|---|
| EP | 0418564 A1 | 3/1991 |
| JP | 5-41602 | 6/1993 |
| WO | 9504528 A2 | 2/1995 |
| WO | 9507104 A1 | 3/1995 |

OTHER PUBLICATIONS

Breslin, Paul A.S., et al., "Ibuprofen as a Chemesthetic Stimulus: Evidence of a Novel Mechanism of Throat Irritation", Chem, Senses, 2001, vol. 26, pp. 55-65.

Hildebrand, Gesine E., et al., "Ketoprofen Sodium: Preparation and Its Formation of Mixed Crystals with Ketoprofen", Journal of Pharmaceutical Sciences, 1997, vol. 86, No. 7, pp. 854-857.

Mura, P., et al., "Utilization of differential scanning calorimetry as a screening technique to determine the compatibility of ketoprofen with excipients", International Journal of Pharmacuetics, 1995, vol. 119, pp. 71-79.

Singhai, A. K., et al., "Cosolvent solubilization and formulation of an aqueous injection of ketoprofen", Pharmazie, 1996, vol. 51, pp. 737-740.

Sridevi, Surapanini, et al., "Optimized transdermal delivery of ketoprofen using pH and hydroxypropyl-β-cyclodextrin as co-enhancers", European Journal of Pharmaceutics and Biopharmaceutics, 2002, vol. 54, pp. 151-154.

* cited by examiner

*Primary Examiner* — John Pak
*Assistant Examiner* — Nathan W Schlientz
(74) *Attorney, Agent, or Firm* — Larson & Anderson, LLC

(57) ABSTRACT

A solid dosage form containing a taste masked active agent is provided. The solid dosage form may be provided as a water soluble film that is disintegrable in the oral cavity to deliver and release the taste masked active agent. The disintegrable film includes at least one water soluble polymer and a taste masked ketoprofen active. Also provided are methods for preparing the solid dosage form and for using the solid dosage to administer an effective dosage of an active agent, such as ketoprofen, into the oral cavity for absorption.

26 Claims, No Drawings

SOLID DOSAGE FORM CONTAINING A TASTE MASKED ACTIVE AGENT

This application claims the benefit of U.S. Provisional Application 60/783,189 filed Mar. 16, 2006.

The present invention relates to dosage forms for the delivery and release of an active agent. According to certain embodiments, the solid dosage form comprises a disintegrable oral film or orally disintegrating tablet for the delivery and release of a pharmacologically active agent into the oral cavity. According to further embodiments, the disintegrable oral film contains a taste masked ketoprofen active for release into the oral cavity. The oral film containing the taste masked ketoprofen does not have a bitter taste nor does it irritate the throat.

BACKGROUND

Ketoprofen is a well-known non-steroidal anti-inflammatory drug (NSAID). Ketoprofen is commercially-available in traditional tablet form, which is to be swallowed with liquids. The traditional tablet dosage form may not be appropriate for certain classes of individuals, such as young children or the geriatric population who have difficulty swallowing. Furthermore, the traditional tablet dosage form requires access to water or other potable liquids to aid in the administration of the tablet dosage form.

In an effort to overcome the difficulties associated with self-administration of the traditional tablet dosage form, orally disintegrating dosage forms, such as thin films or orally disintegrating tablets for delivering a pharmacologically active agent via the oral cavity have been developed. The thin films are generally thin strip solid dosage forms incorporating a pharmacologically active agent, and which disintegrate in the oral cavity to release the active agent that is incorporated in the film. A wide variety of pharmacologically active agents have been incorporated into disintegrable thin film dosage forms.

Ketoprofen is a propionic acid derivative and has an unpleasant bitter taste. Ketoprofen is also known to irritate the throat mucosa. Accordingly, disintegrable ketoprofen-containing oral thin film or disintegrable oral tablet dosage forms would be considered by those having ordinary skill in the art to be undesirable as being unpalatable.

U.S. Patent Application Publication No. 2002/0169212 discloses a stable solution of ketoprofen in water for mass medicating animals. The solution is prepared by mixing ketoprofen with an edible weak base and water. The edible weak base is used in combination with ketoprofen in a ratio of 10 to 1 to completely and rapidly solubilize the ketoprofen in cold water. It is disclosed that flavoring or sweetening agents are added to the ketoprofen solution to increase the palatability of the solution. This publication, however, does not disclose or suggest a solid dosage form containing a taste masked ketoprofen active.

Thus, there remains a need in the art for solid dosage forms, such as disintegrating oral films, that deliver an effective dose of the pharmacologically active agent ketoprofen to the oral cavity, and which are not accompanied by the usual bitter taste of ketoprofen or irritation to the oral and throat mucosa.

SUMMARY

A solid dosage form is provided, said solid dosage form comprises a pharmacologically effective amount of a ketoprofen active, an edible alkaline agent and a pharmaceutically acceptable carrier.

According to certain embodiments, the solid dosage form comprises a disintegrable oral film comprising a pharmacologically effective amount of a ketoprofen active, an edible alkaline agent, and at least one water soluble film forming polymer.

A method for preparing a solid dosage form is also provided, the method comprises mixing a pharmacologically effective amount of a ketoprofen active, an edible alkaline agent, and a pharmaceutically acceptable carrier to form a mixture, and forming a solid dosage form from the mixture.

According to certain embodiments, a method of preparing a disintegrable oral film is provided, the method comprises preparing a mixture comprising a ketoprofen active, and edible alkaline agent for increasing the pH of the mixture, and a liquid, combining the mixture with at least one film forming polymer to form a polymer mixture, and forming a film from the polymer mixture.

According to alternative embodiments, the method for preparing a disintegrable oral film comprises mixing a ketoprofen active, at least one film forming polymer, and a liquid to form a mixture, increasing the pH of the mixture with an edible alkaline agent, and forming a film from the mixture.

According to further alternative embodiments, the method for preparing a disintegrable oral film comprises mixing at least one film forming polymer and a liquid to form a mixture, adding an edible base increasing the pH of the mixture, adding a ketoprofen active to the mixture, and forming a film from the mixture.

According to further embodiments, a method of administering an active agent is provided, the method comprises providing a solid dosage form comprising a taste masked ketoprofen active, and introducing said solid dosage form into the oral cavity.

According to certain embodiments, the method of administering an active agent comprises providing a disintegrable oral film comprising a taste masked ketoprofen active, and introducing said film into the oral cavity.

DETAILED DESCRIPTION

A solid dosage form, such as a disintegrable oral film, for delivering and releasing a pharmacologically active agent into the oral cavity is provided. The solid dosage form comprises a pharmacologically effective amount of a ketoprofen active, and edible alkaline agent or base, and a pharmacologically acceptable carrier. The edible alkaline agent or base material is included in an amount effective to increase the pH of the mixture comprising a ketoprofen active, which results in taste masking of the ketoprofen active. The disintegrating oral film delivers and releases a pharmacologically effective amount of the taste masked ketoprofen active agent to the oral cavity.

According to certain embodiments, the oral film compositions for the delivery and release of a pharmacologically active agent contains at least one film-forming agent, an edible alkaline agent or base, and a pharmacologically effective amount of a ketoprofen agent for delivery and release into the oral cavity of an individual so that the ketoprofen active may be absorbed.

The dosage form may be a monolayer or multi-layer film, which comprises at least one water soluble film forming polymer, an edible alkaline agent or base, and a pharmacologically effective amount of a taste masked ketoprofen active. The film disintegrates when applied to the oral cavity to release the taste masked ketoprofen active agent, which is then swallowed to be absorbed.

The oral film comprises at least one water soluble film forming polymer. Water soluble film forming polymers that are suitable for use in the preparation of the disintegrating oral films include, but are not limited to, cellulose, cellulose derivatives, polyalkylene oxides, polyalkylene glycols, synthetically or naturally occurring gums, acrylic acid polymers, acrylic acid copolymers, methacrylic acid polymers, methacrylic acid copolymers, polyacrylamides, carrageanan, pullunan, polyvinyl pyrrolidone, polyvinyl alcohol, alginic acid, salts of alginic acid, carboxyvinyl polymers and mixtures thereof.

Without limitation, suitable cellulose derivatives that may be used to prepare the disintegrating oral films include alkyl celluloses, such as methyl cellulose and ethyl cellulose, substituted alkyl celluloses, such as hydroxyethyl cellulose, hydroxypropyl cellulose, hydroxypropyl methylcellulose, carboxymethyl cellulose, salts of substituted alkyl celluloses, such as sodium carboxymethyl cellulose and mixtures thereof.

Without limitation, suitable gums that may be used to prepare the disintegrating oral films include xanthan gum, tragacanth gum, guar gum, acacia gum, arabic gum and mixtures thereof.

According to certain embodiments, the film forming polymers may be present in the dry oral film in an amount from about 5 weight percent (wt %) to about 75 wt %, based on the total weight of the dry oral film. According to other embodiments, the film forming polymers may be present in the dry film in an amount from about 10 wt % to about 60 wt %, based on the total weight of the dry oral film. According to further embodiments, the film forming polymers may be present in the dry film in an amount from about 20 wt % to about 40 wt %, based on the total weight of the dry oral film.

According to certain illustrative embodiments, the disintegrable oral film comprises a mixture of hydroxypropyl methylcellulose polymers and/or hydroxypropyl polymers. Without limitation, a suitable hydroxypropyl cellulose polymer for use in the oral film is commercially-available from the Aqualon Division of Hercules under the trademark KLUCEL. KLUCEL hydroxypropyl cellulose polymers are non-ionic, water soluble cellulose ether polymers that are formed by the reaction of cellulose with propylene oxide. KLUCEL polymers are soluble in variety of polar solvents and water. KLUCEL polymers are safe and effective for use in pharmaceutical applications.

Hydroxypropyl methylcellulose polymers for use in the preparation of the disintegrating oral films are commercially-available from The Dow Chemical Company under the trademark METHOCEL. A particularly suitable METHOCEL polymer that may be used in the oral film is METHOCEL E50. METHOCEL E50 is a hydroxypropyl methylcellulose polymer having an approximate molecular weight of 30,000. Another suitable METHOCEL polymer that may be used in the oral film is METHOCEL E5. Additionally, hydroxypropyl methycellulose polymers for use in the preparation of the oral film can be commercially obtained from Aqualon Division of Hercules under the trademark BENECEL. Many other commercial sources of hydroxypropyl cellulose and hydroxypropylmethyl cellulose are available and a person having ordinary skill in the art can easily select a suitable source of hydroxypropyl cellulose and hydroxypropyl methylcellulose polymers.

The disintegrating oral films comprise at least one taste masked ketoprofen active in an amount sufficient to reduce or alleviate pain. The term "taste masked ketoprofen" refers to an altered ketoprofen active having a taste characteristic that is different from the taste characteristic of the unaltered ketoprofen active. According to the methods described, taste masking of the ketoprofen active is achieved by increasing the pH of the ketoprofen active with an effective amount of a pharmacologically acceptable and edible alkaline agent or base.

Any pharmacologically acceptable pH increasing agent may be utilized to increase the pH of the ketoprofen active. By way of illustration, and not in limitation, suitable agents that may be utilized to increase the pH of the ketoprofen active include hydroxides, edible bicarbonates, edible carbonates, buffers and mixtures thereof.

Suitable edible bicarbonates include, without limitation, alkali metal bicarbonates, such as sodium bicarbonate and potassium bicarbonate.

Suitable edible carbonates include, without limitation, alkali metal carbonates, such as calcium carbonate, sodium carbonate and potassium carbonate.

Without limitation, sodium hydroxide, calcium hydroxide, magnesium hydroxide, potassium hydroxide and mixtures thereof may be the hydroxide(s) used to increase the pH of the ketoprofen active.

Buffering agents, such as, without limitation, phosphate buffers and citrate buffers may also be utilized to increase the pH of the ketoprofen active. Suitable citrate or phosphate buffers include, without limitation, alkali metal citrate buffers and alkali metal phosphate buffers.

Without limitation, alkaline amino acids, such as arginine and lysine may be utilized to increase the pH of the ketoprofen active in order to prepare a solid dosage form containing a pharmacologically effective amount of a taste masked ketoprofen active.

In certain embodiments, the amount of ketoprofen active included in the oral film is from about 3 mg to about 75 mg per dose unit. According to other embodiments, the amount of the ketoprofen active included in the oral film is from about 10 mg to about 75 mg per dose unit. According to further embodiments, the amount of ketoprofen active included in the oral film is from about 25 mg to about 75 mg per dosage unit. Further illustrative embodiments of the oral film include ketoprofen in an amount of about 3 mg to about 25 mg per dosage unit or from about 10 mg to about 15 mg ketoprofen per dosage unit. Notwithstanding these illustrative dosages, one having ordinary skill in the art may easily select other pharmacologically effective dosages of ketoprofen as required per unit dosage form.

The disintegrable oral films may contain one or more of the following optional components: additional taste modifying agents, bioadhesive agents, buffering agents, coloring agents, stabilizing, agents, inert fillers, emulsifying agents, permeation enhancers, plasticizers and preservatives.

Without limitation, suitable additional taste modifying agents for use in the disintegrable oral film include flavorants, sweeteners, and mixtures thereof. Suitable taste modifying agents include, but are not limited to, the essential oils or water soluble extracts of menthol, wintergreen, peppermint, sweet mint, spearmint, vanillin, cherry, butterscotch, chocolate, cinnamon, clove, lemon, orange, raspberry, rose, spice, violet, herbal, fruit, strawberry, grape, pineapple, vanilla, peppermint, peach, kiwi, papaya, mango, coconut, apple, coffee, plum, watermelon, nuts, green tea, grape fruit, banana, butter, chamomile, sugar, dextrose, lactose, mannitol, sucrose, sucralose, xylitol, malitol, aspartame, saccharin, sorbitol, sodium saccharin, sodium cyclamate, acesulfame, honey and mixtures thereof.

Without limitation, suitable colorants for use in the disintegrable oral film include pigments, dyes, natural food colors that are suitable for food and drug applications, such as FD&C coloring agents and mixtures thereof.

Without limitation, a suitable stabilizing agents for use in the oral thin films include chelating agents. Chelating agents are used to prevent oxidation of the disintegrable oral film. A particularly useful chelating agent is ethylenediaminetetraacetic acid (EDTA). Any chelating agents that can be incorporated into a solid pharmaceutical preparation may be utilized in the oral film.

The oral film compositions may optionally include one or more water soluble inert fillers. Without limitation, suitable water soluble inert fillers for use in the disintegrable oral film include mannitol, xylitol, glucose, fructose, sucrose, sucralose, lactose, trehalose, maltodextrin, dextran, dextrin, modified starches, dextrose, sorbitol, dextrates and mixtures thereof.

Without limitation, suitable emulsifying agents for use in the disintegrable oral film include solubilizers, wetting agents and release modifiers. Suitable emulsifying agents include, but are not limited to, castor oil derivatives, cetyl alcohol, ethanol, hydrogenated vegetable oils, polyvinyl alcohol, simethicone, sorbitan ester, glyceryl monostearate, polyoxyethylene alkyl ethers, polyoxyethylene stearates, poloxamer and mixtures thereof.

The oral film compositions may optionally include at least one plasticizer. Suitable plasticizers which may be included in the film composition include, but are not limited to, alkylene glycols, polyalkylene glycols, glycerol, triacetin, deacetylated monoglyceride, polyethylene glycol, diethyl salate, triethyl citrate and the like.

The oral films may also optionally include one or more "permeation enhancers". A "permeation enhancer" is a natural or synthetic compound which facilitates the absorption of an active agent through a mucosal surface. The phrase "one or more" is intended to mean that a single permeation enhancer, or combinations or mixtures of more than one permeation enhancer, may be included in the oral film.

The oral film composition may also include one or more preservatives. Suitable preservative include, but are not limited to, butylated hydroxyanisole (BHA), butylated hydroxytoluene (BHT), parabens, derivatives of parabens, sorbic acid, salts of sorbic acid, sodium benzoate, propionic acid, salts of propionic acid, acetic acid, salts of acetic acid and mixtures thereof.

Methods for preparing a solid dosage form comprise combining a pharmacologically effective amount of a ketoprofen active with an edible alkaline agent or base and a pharmaceutically acceptable carrier is provided. According to certain embodiments, a method for preparing a disintegrable oral film containing a taste masked ketoprofen active is provided. The method for preparing a disintegrable oral film containing a taste masked ketoprofen active includes preparing a mixture comprising a ketoprofen active and a liquid, increasing the pH of the mixture by the addition of a base or alkaline material, mixing the mixture with at least one film forming polymer to form a polymer mixture, and forming a film from the polymer mixture.

An alternative method for preparing an oral film containing a taste masked ketoprofen active includes mixing the ketoprofen active with at least one film forming polymer to form a mixture in a liquid, increasing the pH of this mixture by the addition of a base or alkaline material, and forming a film from the mixture.

A further illustrative method for preparing an oral film containing a taste masked ketoprofen active includes adding at least one film forming polymer to a liquid to form a mixture, increasing the pH of the mixture of the film forming polymer and liquid, adding a ketoprofen active to the mixture either by itself or mixed in a liquid, and forming a film from the mixture. Without limitation, the liquid may be water, a hydroalcoholic solution, or an alcohol.

The homogenous mixture of film components is degassed and uniformly coated onto a casting substrate with a predetermined thickness and then dried. Alternatively, the homogenous mixture may be extruded to form a film on a casting substrate. The dried film prepared from casting or extrusion is cut into various sizes to produce individual dosage units. The dried film may be cut by any known cutting method, such as, for example, die cutting, knife cutting or machine cutting.

Ketoprofen suspensions in water generally have a pH of about 3.9. In order to eliminate the bitter taste and throat irritation caused by ketoprofen, the pH of the ketoprofen is adjusted to a pH of about 5.5 or greater. According to certain embodiments, the pH of the ketoprofen is adjusted to a pH in the range of about 5.5 to about 9. According to further embodiments, the pH of the ketoprofen is adjusted to a pH in the range of about 6.5 to about 8.5. According to further embodiments, the pH of the ketoprofen is adjusted to a pH in the range of about 6.6 to about 8.2.

Methods of using the disintegrable film for administering a pharmacologically effective dose of a ketoprofen active to the oral cavity of an individual is also provided. According to illustrative embodiments, the method includes using the disintegrable film to administer an effective dose of a taste masked ketoprofen active to the oral cavity of an individual to alleviate symptoms associated with inflammation and pain. By way of illustration, but not in limitation, the oral thin film containing a taste masked ketoprofen active may be used to administer a pharmacologically active amount of ketoprofen to treat symptoms associated with osteoarthritis, acute tendonitis, bursitis and like conditions.

The thin film dosage form is applied to the oral cavity and may adhere to mucosal surfaces, such as the cheek, palate or tongue as soon as the individual closes his or her mouth. The film disintegrates and releases the ketoprofen active for absorption.

EXAMPLES

The following examples are set forth to further illustrate the oral films and methods of preparation. The below examples, however, should not be construed as limiting the present invention in any manner.

Example 1

A taste masked ketoprofen solution was prepared. Briefly, 100 mg of ketoprofen was added to approximately 1.2 g of 0.5 N NaOH to form a clear solution. The ketoprofen solution was diluted to 95 mL using distilled water. The pH of the diluted solution was adjusted to a pH of 6.62 using 1 N HCl and 0.5 N NaOH. The pH adjusted solution of ketoprofen had little or no bitter taste or throat irritation.

Example 2

A taste masked ketoprofen solution was prepared as in Example 1. Briefly, 100 mg of ketoprofen was added to approximately 1.2 g. of 0.5 N NaOH to form a clear solution. The ketoprofen solution was diluted to 95 mL using distilled water. The pH of the diluted solution was adjusted to a pH of 6.62 using 1 N HCl and 0.5 N NaOH. The pH of the solution was adjusted to a pH of 8.15 using 1% (w/v) sodium bicarbonate. The pH adjusted solution of ketoprofen had little or no bitter taste or throat irritation.

Example 3

A taste masked ketoprofen solution was prepared. Briefly, 1 g of ketoprofen was added to approximately 12.4 g of 0.5 N NaOH to form a clear solution. The solution was diluted to 500 mL with distilled water and the pH was adjusted to a pH of 6.6 using 1 N HCl and 0.5 N NaOH. The pH adjusted solution of ketoprofen had little or no-bitter taste or throat irritation.

Example 4

A taste masked ketoprofen solution was prepared as in Example 2. Briefly, 1 g of Ketoprofen was added to approximately 12.4 g of 0.5 N NaOH to form a clear solution. The solution was diluted to 500 mL with distilled water and the pH was adjusted to a pH of 6.6 using 1 N HCl and 0.5 N NaOH. The pH of the solution was adjusted to a pH or 8.15 using 5% (w/v) sodium bicarbonate. The pH adjusted solution of ketoprofen had little or no bitter taste or throat irritation.

Control Example 5

A disintegrable oral film containing a ketoprofen active and the sweetening agents sorbitol and sucralose was produced from the following formula of ingredients:

| Ingredient | Grams |
| --- | --- |
| Methocel E5 | 5.4 |
| Methocel E50 | 9.8 |
| Klucel JF | 2.9 |
| Maltrin M180 | 6.8 |
| Instant Pure Coat B793 | 6.5 |
| Sorbitol | 6.5 |
| PEG 400 | 8.4 |
| Avicel PH102 | 6.2 |
| Sucralose | 9.7 |
| Cinnamon Flavor | 0.8 |
| FD&C Red #40 | 0.15 |

Ketoprofen was added to the above mixture of ingredients. The pH of the ketoprofen solution was 3.78. The mixture was cast onto a suitable paper substrate and was dried. The film was analyzed and cut to obtain a dosage form containing 4 mg of ketoprofen active. The overall weight of the oral film containing 4 mg of ketoprofen was 36.4 g.

Example 6

A disintegrable oral film containing a taste masked ketoprofen active was produced from the following formula of ingredients:

| Ingredient | Grams |
| --- | --- |
| Methocel E5 | 5.4 |
| Methocel E50 | 9.8 |
| Klucel JF | 2.9 |
| Maltrin M180 | 6.8 |
| Instant Pure Coat B793 | 6.5 |
| Sorbitol | 6.5 |
| PEG 400 | 8.4 |
| Avicel PH102 | 6.2 |
| Sucralose | 9.7 |
| Cinnamon Flavor | 0.8 |
| FD&C Red #40 | 0.15 |

Ketoprofen was added to the above mixture of ingredients. The pH of the ketoprofen solution was adjusted to 8.02 using NaOH, NaHCO$_3$ and HCl. The mixture was cast onto a suitable paper substrate and was dried. The film was analyzed and cut to obtain a dosage form containing 4 mg of ketoprofen active. The overall weight of the oral film containing 4 mg of ketoprofen was 42.8 g.

The ketoprofen-containing thin films prepared in accordance with Examples 5 and 6 above were tested for palatability. Each thin film was tested using eight volunteers. The following numbers were assigned to the assess the degree of irritation to the palate:

| Description | Number |
| --- | --- |
| Not irritating | 0 |
| Slightly irritating | 1 |
| Irritating | 2 |
| Very Irritating | 3 |
| Extremely Irritating | 4 |

The results of the palatability testing for the thin films prepared in accordance with Examples 5 and 6 were as follows:

| | Example 5 | Example 6 |
| --- | --- | --- |
| pH | 3.78 | 8.02 |
| Test Subject A | 3 | 1 |
| Test Subject B | 2 | 0 |
| Test Subject C | 1 | 1 |
| Test Subject D | 1 | 0 |
| Test Subject E | 2 | 0 |
| Test Subject F | 2 | 0.5 |
| Test Subject G | 1 | 1 |
| Test Subject H | 2 | 1 |
| Average | 1.75 | 0.56 |

On average, the oral films containing a non-taste masked ketoprofen active agent was greater than three times more irritating, as compared to an oral film containing a taste masked ketoprofen active. These results clearly demonstrate the palatability of an oral thin film containing a taste masked ketoprofen active.

Example 7

A disintegrable oral film containing a taste masked ketoprofen active was produced from the following formula of ingredients:

| Ingredient | Grams |
| --- | --- |
| Methocel E5 | 1.368 |
| Methocel E50 | 2.47 |
| Klucel JF | 0.722 |
| Maltrin M180 | 1.71 |
| Instant Pure Coat B793 | 1.71 |
| Sucralose | 2.47 |
| Sorbitol | 1.634 |

| Ingredient | Grams |
| --- | --- |
| PEG 400 | 2.128 |
| Avicel PH102 | 1.568 |
| Cherry Flavor | 0.19 |
| FD&C Red #40 | 0.038 |
| Water | 47.348 |

47.348 g of deionized water was placed into a stainless steel pot and heated on a hot plate to 80° C. with mixing. To the water solution, 0.038 g of FD&C Red #40 coloring agent, 1.368 g of METHOCEL E5, 2.47 g of METHOCEL E50, 0.722 g of KLUCEL JF, 1.17 g of Maltrin M180, and 1.71 g of Instant Pure Coat B793 were added, and was mixed at a high mixing speed. The stainless steel pot was removed from the hot plate and transferred to a water bath and cooled. Once the mixture had cooled, the stainless steel pot was removed from the water bath and placed into an ice bath and mixed. The stainless steel pot was removed from the ice bath, and 2.47 g of sucralose, 1.634 g of sorbitol-2.128 g of PEG 400, 0.19 g of cherry flavor, 1.568 g of AVICEL PH 102 was added with mixing.

A ketoprofen solution was prepared by adding 7.2 g to enough 0.5 N NaOH to get the 7.2 g of the ketoprofen into solution. The ketoprofen solution was added to the mixture of film ingredients. The pH of the thin film mixture containing the ketoprofen solution was adjusted to 6.7 with 1 N HCl. A 5% (w/v) solution of sodium bicarbonate was then used to adjust the pH of the complete mixture to 7.7.

The oral film containing the ketoprofen and with pH adjustment tasted sweet. The film did not possess any bitter taste and did not cause any throat irritation.

The disintegrable oral films are useful to deliver a pharmacologically active dose of ketoprofen to an individual. The disintegrable oral films may be self-administered by an individual as needed to alleviate pain and discomfort associated with inflammation.

While the taste masked ketoprofen active-containing solid dosage form has been described with respect to illustrative disintegrating oral film embodiments, a taste masked ketoprofen active may be incorporated into a wide variety of pharmacologically acceptable solid dosage forms. For example, a taste masked ketoprofen active may be incorporated into an orally disintegrating tablet dosage form. Such orally disintegrating tablets, unlike the traditional tablet dosage form, rapidly disintegrates in the oral cavity and releases the active to be swallowed.

A ketoprofen mixture comprising ketoprofen and an edible alkaline agent can be incorporated into orally disintegrating tablets. The orally disintegrating tablets may be prepared using several illustrative methods.

According to one illustrative embodiment, the orally disintegrating tablets may be prepared by forming a mixture of water soluble or water dispersible substances such as polymers or saccharides. The ketoprofen may be incorporated into this mixture along with an edible alkaline agent to adjust the pH above 5.5. This mixture may be lyophilized to form a matrix which can easily disintegrate in presence of water due to the porous nature of the lyophilized pellet.

Alternately, the liquid in the mixture may be evaporated by heating or vacuum drying. Instead of water, alcoholic or hydroalcoholic solvents can be also used. Materials such as gelatin, dextran, dextrin, alginates, polyvinyl alcohol, polyvinylpyrrolidone, saccharides, trehalose, mannitol, sorbitol, erythritol, celluloses, agar or combinations of them can be used to prepare the orally disintegrating tablet containing ketoprofen that is palatable without throat irritation or bitterness. As with the disintegrating oral film, a wide variety of optional ingredients may be added, such as flavors and sweeteners to improve the taste of the orally disintegrating tablet.

According to further illustrative embodiments, an orally disintegrating tablet containing a ketoprofen active may be prepared by providing pharmacologically acceptable powder(s) capable of being compressed into an orally disintegrating tablet form, and combining the ketoprofen having an increased pH with the powder. The powder having the ketoprofen mixture added thereto is then compressed into an orally disintegrating tablet dosage form. By way of illustration, sugar alcohols or saccharides, such as mannitol, xylitol, maltitol, lactitol, erythritol, xylitol, sorbitol, fructose, lactose, glucose, sucrose, trehalose, dextrose, maltose, isomalt, starch hydrolysate, polydextrose along with optionally celluloses or disintegrants, such as crosspovidone, crosscarmellose sodium, low substituted hydroxypropycellulose can be compressed to form an orally disintegrating tablet dosage form. A ketoprofen mixture in a liquid containing an edible alkaline material to obtain pH above 5.5 can be added to the powder mixture. The ketoprofen mixture may be applied to the powder mixture by spraying and mixing the powders. The addition of the ketoprofen mixture may occur during granulation of the powders. This mixture of powder and ketoprofen active may then be directly compressed into a disintegrable oral tablet. Lubricants, such as stearic acid and magnesium stearate, may be optionally added before or during the compression process. Flavoring and sweetening agents may also be added to aid in the palatability of the orally disintegrating tablet.

Variations of above processes in preparing orally disintegrating table may be carried out. Irrespective of the specific process and composition in preparing orally disintegrating tablet, based on the description herein, one skilled in the art could add ketoprofen along with an edible alkaline agent to obtain an orally disintegrating table having good palatability.

While the present invention has been described above in connection with the certain illustrative embodiments, it is to be understood that other similar embodiments may be used or modifications and additions may be made to the described embodiments for performing the same function of the present invention without deviating therefrom. Furthermore, all embodiments disclosed are not necessarily in the alternative, as various embodiments of the invention may be combined to provide the desired characteristics. Variations can be made by one having ordinary skill in the art without departing from the spirit and scope of the invention. Therefore, the present invention should not be limited to any single illustrative embodiment, but rather construed in breadth and scope in accordance with the recitation of the attached claims.

We claim:
1. A solid dosage form comprising:
(a) an edible alkaline agent;
(b) a pharmacologically effective amount of a ketoprofen active; and
(c) a pharmaceutically acceptable carrier, wherein said solid dosage form is a disintegrable thin strip oral film obtained from a mixture having a pH of about 6 to about 9, wherein said edible alkaline agent is a hydroxide selected from the group consisting of sodium hydroxide, calcium hydroxide, magnesium hydroxide, and potassium hydroxide and is present in sufficient amount to mask bitter taste.

2. The solid form dosage form of claim 1, wherein said pharmaceutically acceptable carrier comprises at least one water soluble film forming polymer.

3. The solid dosage form of claim 2, wherein said water soluble film forming polymer is selected from the group consisting of cellulose, alkyl celluloses, substituted alkyl celluloses, salts of substituted alkyl celluloses, polyalkylene oxides, polyalkylene glycols, synthetically or naturally occurring gums, acrylic acid polymers, acrylic acid copolymers, methacrylic acid polymers, methacrylic acid copolymers, polyacrylamides, carrageenan, pullunan, polyvinyl pyrrolidone, polyvinyl alcohol, alginic acid, salts of alginic acid, carboxyvinyl polymers and mixtures thereof.

4. The solid dosage form of claim 3, wherein said water soluble film forming polymer is a substituted alkyl cellulose.

5. The solid dosage form of claim 4, wherein said substituted alkyl cellulose is selected from the group consisting of hydroxyethyl cellulose, hydroxyproply cellulose, hydroxypropyl methylcellulose, carboxymethyl cellulose and mixtures thereof.

6. The solid dosage form of claim 5, wherein said substituted alkyl cellulose is hydroxypropyl methylcellulose.

7. The solid dosage form of claim 5, wherein said film forming polymer is a mixture of at least two different hydroxylpropyl methylcellulose polymers.

8. The solid form of claim 7, wherein said solid dosage form further comprises at least one agent selected from the group consisting of bioadhesive agents, coloring agents, stabilizing agents, inert fillers, emulsifying agents, permeation enhancers, plasticizers, preservatives and mixtures thereof.

9. A method for the treatment of osteoarthritis comprising administering the thin strip oral film of claim 1.

10. A method for the treatment of acute tendinitis comprising administering the thin strip oral film of claim 1.

11. A method for the treatment of bursitis comprising administering the thin strip oral film of claim 1.

12. A method for the analgesic treatment comprising administering the thin strip oral film of claim 1.

13. A method for preparing a solid dosage form comprising forming a mixture of an edible alkaline agent, a pharmacologically effective amount of a ketoprofen active, and a pharmaceutically acceptable carrier, wherein said edible alkaline agent is a hydroxide selected from the group consisting of sodium hydroxide, calcium hydroxide, magnesium hydroxide, and potassium hydroxide and is present in the mixture in sufficient amount to mask the bitter taste of the ketoprofen active, and wherein the mixture has a pH of about 6 to about 9; and forming a solid dosage form from the mixture wherein the solid dosage form is a disintegrable thin strip oral film.

14. The method of preparing a solid dosage form of claim 13, comprising the steps of:
(a) preparing a solution comprising the ketoprofen active and a liquid to form a ketoprofen solution;
(b) adjusting the pH of the ketoprofen solution by adding the edible alkaline agent to form a pH-adjusted mixture;
(c) mixing the pH-adjusted mixture with at least one water soluble film forming polymer to form a polymer mixture; and
(d) forming a disintegrable thin strip oral film from the polymer mixture.

15. The method of preparing a solid dosage form of claim 14, wherein said liquid is water.

16. The method of preparing a solid dosage form of claim 14, wherein said pH of said ketoprofen solution is adjusted to a pH of about 6.5 to about 8.5.

17. The method of preparing a solid dosage form of claim 14, wherein said water soluble film forming polymer is selected from the group consisting of cellulose, alkyl celluloses, substituted alkyl celluloses, salts of substituted alkyl celluloses, polyalkylene oxides, polyalkylene glycols, synthetically or naturally occurring gums, acrylic acid polymers, acrylic acid copolymers, methacrylic acidpolymers, methacrylic acid copolymers, polyacrylamides, carrageenan, pullunan, polyvinyl pyrrolidone, polyvinyl alcohol, alginic acid, salts of alginic acid, carboxyvinyl polymers and mixtures thereof.

18. The method of preparing a solid dosage form of claim 17, wherein said water soluble film forming polymer is a substituted alkyl cellulose.

19. The method of preparing a solid dosage form of claim 18, wherein said substituted alkyl cellulose is selected from the group consisting of hydroxethyl cellulose, hydroxypropyl cellulose, hydroxypropyl methylcellulose, carboxymethyl cellulose and mixtures thereof.

20. The method of preparing a solid dosage form of claim 19, wherein said substituted alkyl cellulose is hydroxypropyl methylcellulose.

21. The method of preparing a solid dosage form of claim 19, wherein said water soluble film forming polymer is a mixture of at least two hydroxypropyl methylcellulose polymers.

22. The method of claim 13 comprising:
(a) mixing the ketoprofen active with at least one film forming polymer and a liquid to form a liquid-containing mixture;
(b) increasing the pH of the liquid-containing mixture by adding the edible alkaline agent; and
(c) forming a film from the liquid-containing mixture.

23. The method of claim 13 comprising:
(a) mixing at least one film forming polymer and a liquid to form a liquid-containing mixture;
(b) increasing the pH of the liquid-containing mixture by adding the edible alkaline agent; and
(c) adding the ketoprofen active to the liquid-containing mixture.

24. The method of claim 13, wherein the mixture is treated at a temperature of at least 80° C.

25. The method of claim 13, wherein the mixture is degassed prior to forming the solid dosage form.

26. A method of administering an active agent to treat inflammation, pain, osteoarthritis, acute tendinitis, bursitis, or combinations thereof, the method comprising:
(a) providing a solid dosage form disintegrable thin strip oral film comprising pharmacologically effective amounts of a ketoprofen active, an edible alkaline agent, and a pharmacologically acceptable carrier; and
(b) introducing said solid dosage form into the oral cavity, wherein the edible alkaline agent is a hydroxide selected from the group consisting of sodium hydroxide, calcium hydroxide, magnesium hydroxide, and potassium hydroxide and is present in a sufficient amount to mask the bitter taste of the ketoprofen active, and wherein the thin strip oral film is obtained from a mixture having a pH of about 6 to about 9.

* * * * *